(12) United States Patent
Rooney

(10) Patent No.: US 7,727,173 B2
(45) Date of Patent: Jun. 1, 2010

(54) METHOD AND APPARATUS FOR THE TREATMENT OF PLANTAR ULCERS AND FOOT DEFORMITIES

(76) Inventor: John E. Rooney, 24 Windsor Dr., Oak Brook, IL (US) 60523

( * ) Notice: Subject to any disclaimer, the term of this patent is extended or adjusted under 35 U.S.C. 154(b) by 1105 days.

(21) Appl. No.: 11/166,876

(22) Filed: Jun. 24, 2005

(65) Prior Publication Data
US 2005/0240133 A1    Oct. 27, 2005

Related U.S. Application Data

(63) Continuation-in-part of application No. 10/150,693, filed on May 17, 2002, now Pat. No. 6,945,946.

(51) Int. Cl.
*A61F 5/00* (2006.01)
(52) U.S. Cl. .......................... 602/23; 602/27
(58) Field of Classification Search ................ 602/5–8, 602/27–29, 23; 128/882
See application file for complete search history.

(56) References Cited

U.S. PATENT DOCUMENTS

| | | | |
|---|---|---|---|
| 3,916,886 A | 11/1975 | Rogers | |
| 4,184,273 A | 1/1980 | Boyer et al. | |
| 4,351,324 A | 9/1982 | Bronkhorst | |
| 4,641,639 A | 2/1987 | Padilla | |
| 5,068,983 A * | 12/1991 | Marc | 36/44 |
| 5,197,942 A * | 3/1993 | Brady | 602/5 |
| 5,226,245 A | 7/1993 | Lamont | |
| 5,368,551 A | 11/1994 | Zuckerman | |
| 5,370,604 A | 12/1994 | Bernardoni | |
| 5,571,077 A | 11/1996 | Klearman et al. | |
| 5,762,622 A | 6/1998 | Lamont | |
| 5,797,862 A | 8/1998 | Lamont | |
| 5,817,041 A | 10/1998 | Bader | |
| 5,827,210 A | 10/1998 | Antar et al. | |
| 5,833,639 A | 11/1998 | Nunes et al. | |
| 5,853,380 A | 12/1998 | Miller | |
| 6,083,185 A | 7/2000 | Lamont | |
| 6,228,044 B1 | 5/2001 | Jensen et al. | |
| 6,361,514 B1 * | 3/2002 | Brown et al. | 602/23 |
| 6,572,571 B2 | 6/2003 | Lowe | |
| 6,610,897 B2 * | 8/2003 | Cavanagh et al. | 602/54 |
| 2003/0110662 A1 * | 6/2003 | Gilman et al. | 36/43 |

* cited by examiner

Primary Examiner—Michael A. Brown
(74) Attorney, Agent, or Firm—Michael P. Mazza, LLC

(57) ABSTRACT

A custom-made ankle/foot orthosis for the treatment of patients having plantar ulcers and foot deformities is disclosed, which comprises a rigid L-shaped support member and a rigid anterior support shell hingedly articulated to the L-shaped support member. The plantar portion of the L-shaped member further comprises at least one ulcer-protecting hollow spatially located for fitted placement in inferior adjacency to a user's plantar ulcer, thus allowing the user to transfer the user's weight away from the plantar ulcer and facilitating plantar ulcer treatment. The anterior support shell is designed for lateral hinged attachment to the L-shaped member to take advantage of medial tibial flare structure for enhancing the weight-bearing properties of the disclosed orthosis. Leg securement structure attaches the anterior support shell to the L-shaped member in fixed, weight-bearing relation about the proximal, anterior portion of the user's lower leg.

9 Claims, 9 Drawing Sheets

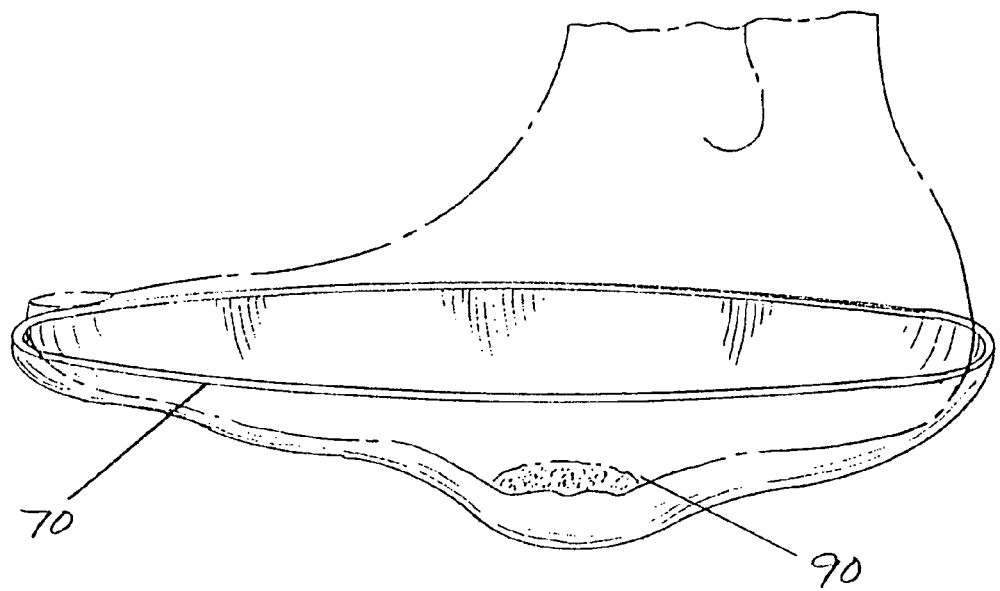
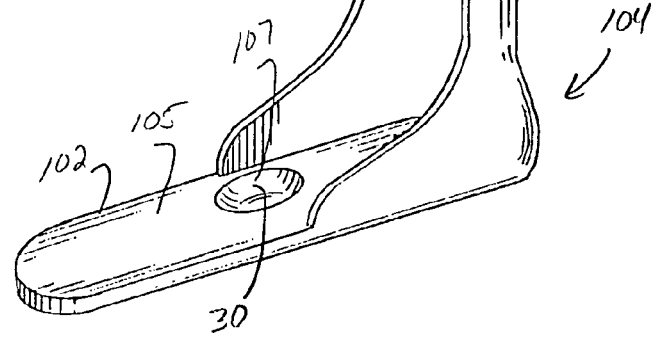

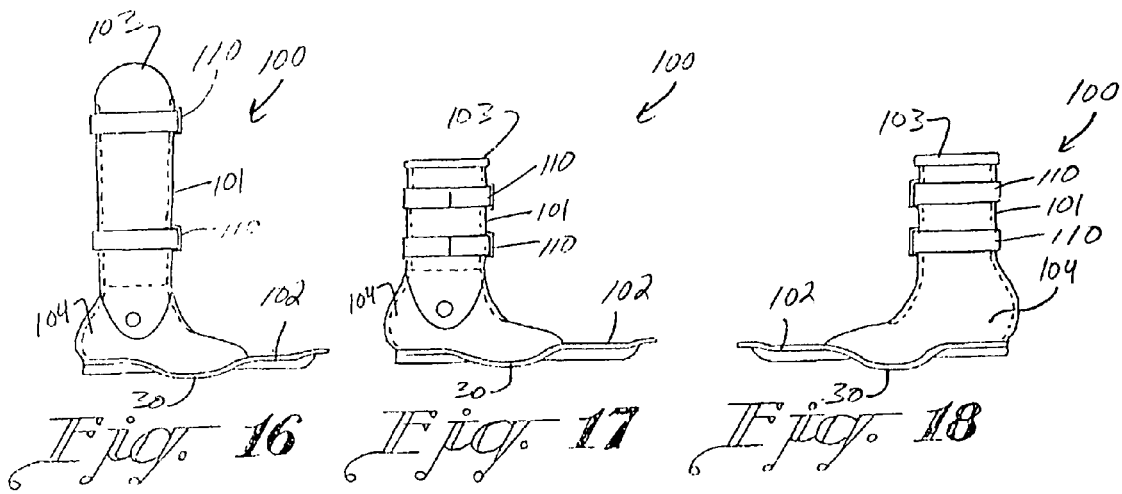
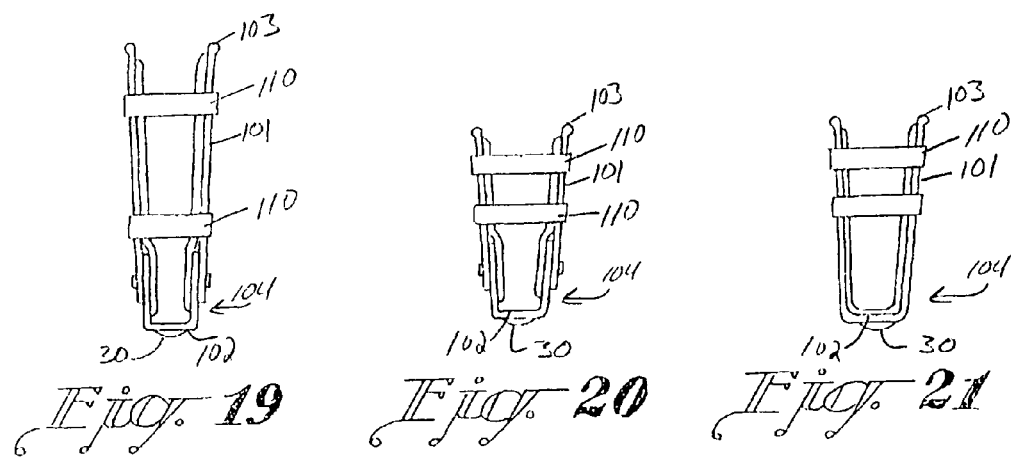
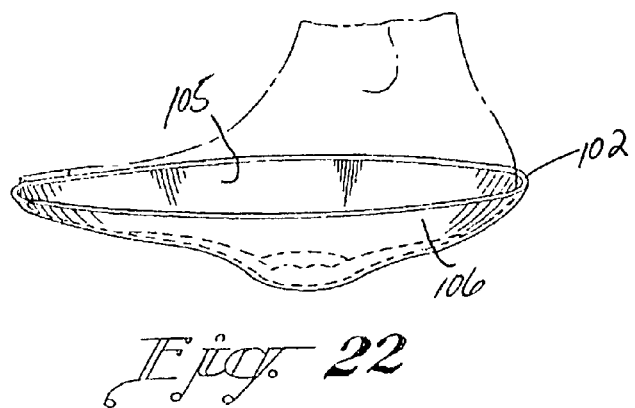

METHOD AND APPARATUS FOR THE TREATMENT OF PLANTAR ULCERS AND FOOT DEFORMITIES

PRIOR HISTORY

This application is a continuation-in-part patent application claiming the benefit of U.S. patent application Ser. No. 10/150,693, filed in the United States Patent and Trademark Office on May 17, 2002 now U.S. Pat. No. 6,945,946.

BACKGROUND OF THE INVENTION

1. Field of the Invention

The present invention relates generally to an apparatus for the treatment of foot conditions, and more particularly, to an orthotic device constructed to unload or transfer weight off of a wounded or ulcerated area of the foot thus aiding in the healing of foot conditions. In its most common usage, the present invention relates to an orthosis for the treatment of diabetic plantar ulcers, whereby body weight is borne by the orthosis to aid in the healing of this plantar skin condition.

2. Description of the Prior Art

Foot ulcers represent one of the most notable risk factors for lower extremity amputations in persons diagnosed with diabetes mellitus. Persons diagnosed with diabetes are typically classified as slow healers and are prone to debilitating foot ulcers due to both neurologic and vascular complications. Peripheral neuropathy can cause altered or complete loss of tactile sensation in the foot and/or leg, and in this regard, the diabetic patient with advanced neuropathy tends to loose the ability to discriminate between sharp-dull tactile sensations. Accordingly, any cuts or trauma to the foot of a diabetic patient with advanced neuropathy often go unnoticed for lengthy periods of time. At present, there is no known cure for neuropathy, although strict control over glucose levels has been shown to slow the progression of the neuropathy.

Further, a deformity commonly known as "charcot foot" occurs as a result of decreased sensation. Patients with "normal" tactile sensation in their feet automatically determine when too much pressure is being placed on an area of the foot. Once identified, the human body instinctively shifts position to relieve the stress. A patient with advanced neuropathy looses this important mechanism. As a result, tissue ischemia and necrosis may occur leading to plantar ulcers. Microfractures in the bones of the foot go unnoticed and untreated, resulting in disfigurement, chronic swelling and additional bony prominences.

Microvascular disease is an additional problem for diabetic patients, which can also lead to foot ulcers. It is well known that diabetes often results in a narrowing of smaller arteries, which narrowing cannot be resolved surgically. This microvascularization thus further prompts the diabetic patient to adhere to a strict glucose level regimen, maintain an ideal body weight and cease tobacco smoking in an attempt to reduce the onset of microvascular disease. Should a diabetic patient develop a plantar ulcer, for whatever reason, treatment options are generally limited to a two-fold treatment plan. In the first instance, the prime objective is to obtain wound closure, which eliminates a portal of entry for bacterial invasion and development of limb-threatening infection. In the second instance, a further objective is to allow for a reduction in sited foot pressures or the "offloading" of tissues. In this regard, protective orthotic footwear has been shown to lower sited foot pressures and further has been shown to contribute to the healing and closing of wounds. Moreover, once a given plantar ulcer has been effectively closed, protective orthotic footwear has been shown to prevent the reoccurrence of plantar ulcers. Orthotic footwear has thus become an area of special interest to a number of industries reliant on the development of treatment devices for medical conditions.

Notably, various orthotic devices for the treatment of plantar ulcers and other foot abnormalities have been developed and are known in the prior art, particularly, for example, patients who have diabetes. A number of the more interesting orthotic devices are disclosed by the following: U.S. Pat. No. 3,916,886, issued to Rogers; U.S. Pat. No. 4,184,273, issued to Boyer et al.; U.S. Pat. No. 4,351,324, issued to Bronkhorst; U.S. Pat. No. 4,461,639, issued to Padilla; U.S. Pat. No. 5,197,942, issued to Brady; U.S. Pat. No. 5,226,245, issued to Lamont; U.S. Pat. No. 5,368,551, issued to Zuckerman; U.S. Pat. No. 5,370,604, issued to Bernardoni; U.S. Pat. No. 5,571,077, issued to Klearman et al.; U.S. Pat. No. 5,762,622, issued to Lamont; U.S. Pat. No. 5,797,862, issued to Lamont; U.S. Pat. No. 5,817,041, issued to Bader; U.S. Pat. No. 5,827,210, issued to Antar, et al.; U.S. Pat. No. 5,833,639, issued to Nunes, et al.; U.S. Pat. No. 5,853,380, issued to Miller; U.S. Pat. No. 6,083,185, issued to Lamont; U.S. Pat. No. 6,228,044, issued to Jensen et al.; U.S. Pat. No. 6,361,514, issued to Brown et al.; and U.S. Pat. No. 6,572,571, issued to Lowe.

More particularly, U.S. Pat. No. 5,368,551 ('551 patent), which issued to Zuckerman, discloses an Ankle Brace Walker. The '551 patent teaches a pair of struts that are frictionally and mechanically engaged with corresponding opposed uprights of the base of an ankle brace walker to provide rigidity to an enveloped foot and ankle. The base includes a plurality of longitudinally aligned, laterally offset flanges intermediate laterally aligned flanges, all of which flanges are disposed intermediate the sole and the foot bed of the base to provide rigidity for the foot and with sufficient strength to permit walking without danger of breakage of the base with resulting injury to a user. Cushioning means and strap means retain the foot and ankle comfortable but firmly within the ankle brace walker.

U.S. Pat. No. 5,817,041 ('041 patent), which issued to Bader, discloses a Rigid Lower Limb Orthotic. The '041 patent teaches a foot orthotic, a pair of lateral supporting members, a detached or removable anterior support member, a posterior support member, and strips of composite materials to resist plantar flexion, dorsiflexion and various of movements of the foot and ankle. The lateral supporting members further have strips of composite materials having fibers orientated substantially parallel to the lengthwise axis of the lateral supporting members. The foot orthotic and posterior supporting member further have composite strips extending across the bottom portion of the foot orthotic and rear side of the posterior supporting member respectively.

U.S. Pat. No. 6,361,514 ('514 patent), which issued to Brown, discloses a Universal Ankle Splint. The '514 patent teaches a universal walking splint movably attachable to the lower leg and foot to substantially immobilize the lower leg and foot. It has a posterior shell for holding a sole insert pad, and a movable and removable arch support attachable to the sole insert pad to allow selective arch support at the proper location under either a right foot or a left foot.

U.S. Pat. No. 6,572,571 ('571 patent), which issued to Lowe, discloses a Limb Stabilizer. The '571 patent teaches means for stabilizing a limb of an animal, an elongated trough-shaped base for supporting the limb, a trough-shaped extension, integrally connected to the base, and extending therefrom at an acute angle relative to the axis of the base. An elongated trough-shaped cover is connectable to the base. Additionally, a curved, trough-shaped support and means for fastening the support to the base are provided.

U.S. Pat. No. 5,197,942 ('942 patent), which issued to Brady, discloses a Customized Foot Orthosis. The '942 patent is designed to be worn by a patient having at least one ulcerated site on his or her foot. The foot orthosis comprises a brace having at least a back portion and a sole portion, an aperture extending through the sole portion, and means for fastening the orthosis securely to the patient's foot and lower leg. The aperture is positioned to correspond with the location of the ulcerated site on the patient's foot which relieves pressure from the ulcerated site when the patient is weight-bearing and thereby permits the patient to be mobile while simultaneously assisting in the aeration and healing of the ulcerated site. The '942 patent, does not disclose the use of a permanent orthosis, which may be easily worn to heal and close a plantar ulcer, and additionally, to maintain the plantar surface in a healed unulcerated state. Further, the '942 patent fails to disclose an orthosis, which may be easily donned and inserted inside a patient's modified street shoe.

U.S. Pat. No. 6,228,044 ('044 patent), which issued to Jensen et al., discloses Methods and Apparatus for Treating Plantar Ulcers. This disclosure teaches a temporarily worn leg brace which comprises a pair of rigid shells, a fastening system for joining the shells together to form a unified brace and a combination of bladders which engage the patient's leg and tarsal region to off-weight the plantar surface, prevent plantar flexing and minimize shearing forces to the plantar surface. The volume of the bladders may be adjusted to maintain a uniform pressure between the bladders and the patient's leg. In addition to providing a means for off-weighting the plantar surface of a patient's foot, the brace is reusable and adjustable to accommodate changes in a patient's leg size. The '044 patent does not disclose the use of a permanent orthosis, which may be easily worn to heal and close a plantar ulcer, and additionally, to maintain the plantar surface in a healed unulcerated state. Further, the '044 patent does not disclose an orthosis, which may be easily donned and inserted inside a patient's modified street shoe.

U.S. Pat. Nos. 5,226,245 ('245 patent); 5,762,622 ('622 patent); 5,797,862 ('862 patent); and 6,083,185 ('185 patent), all of which issued to Lamont, disclose boot structures for use in the treatment of plantar conditions. In this regard, the '245 patent discloses a Protective Boot Structure, which is designed for patients with arterial disease. The boot structure comprises a separate fluid-containing cushion which can be attached in a variety of positions or in the boot to provide support for a patient's foot and leg primarily when bedridden, though a modest amount of ambulatory use is contemplated. The '622 patent discloses a Medical Boot with Unitary Splint. This invention comprises a relatively soft boot component having a foot portion, a leg portion, and a relatively hard plastic splint formed with a foot portion and a leg portion. The foot portion of the splint is mounted inside the boot and the leg portion of the splint is outside the rear surface of the boot. The '862 patent discloses a Medical Boot for Patient with Diabetic Foot. This invention is also designed for patients with arterial disease and comprises an insole formed with a heat-activated material to form a permanent impression of the bottom of the patient's foot. The insole is adapted for removable placement in a medical boot. The '185 patent discloses a Medical Boot for Patient with Diabetic Foot. This disclosure details a liner for use with the invention disclosed in the '245 patent and comprises a cushion placed inside a medical boot against an upper rear portion of the boot, to promote flotation support for the wearer's ankle when the cushion includes a soft midsection panel adapted to engage the ankle rear surface. A deformable fluid-containing pouch is removably disposed in a hollow interior space within the panel to provide ankle support. The pouch can be removed through a rear access opening that is normally closed a by a zipper means for closure. These patents, which issued to Lamont, do not disclose the use of a permanent orthosis, which may be easily worn to heal and close a plantar ulcer, and additionally, to maintain the plantar surface in a healed unulcerated state. Further, the Lamont disclosures fail to disclose an orthosis, which may be easily donned and inserted inside a patient's modified street shoe.

U.S. Pat. No. 5,833,639 ('639 patent), which issued to Nunes et al., discloses a Short Leg Walker. This invention teaches and describes a short leg walker comprising a rigid sole and calf shell and an articulated rigid skin and dorsal shell. The shells are padded at selected locations with a non-inflatable padding such as foam or fiber padding and at other locations with an inflatable bladder and a second bladder between the inflatable bladder and the limb of the patient. The second bladder is responsive to deforming pressure exerted on it and will maintain its support of the limb when the pressure is removed. This construction is intended to be used to immobilize the foot, lower leg and ankle in lieu of a plaster of Paris cast, (See, Col. No. 1, Line Nos. 10-14) and no teaching is found for the treatment of plantar ulcers. The '639 patent, thus, does not disclose the use of a permanent orthosis, which may be easily worn to heal and close a plantar ulcer, and additionally, to maintain the plantar surface in a healed unulcerated state. Further, the '639 patent fails to disclose an orthosis, which may be easily donned and inserted inside a patient's modified street shoe.

U.S. Pat. No. 5,370,604 ('604 patent), which issued to Bernardoni, discloses a Kinesthetic Ankle-Foot Orthosis. This invention has been designed primarily to treat the condition commonly known as "drop foot" in which a patient is unable to lift the patient's foot. The orthosis described in the '604 patent comprises a lower portion, which contacts the plantar surface of the foot. The lower portion is continuous with an upper portion, which contacts the posterior surface of the lower leg. The lower and upper portions are attached to a patient's leg by a strap extending around the proximal portion of a patient's lower leg. The lower portion of the orthosis further comprises apertures at selected locations to allow selected portions of the foot to contact the floor while the orthosis is being used. The '604 patent does not disclose the use of a permanent orthosis, which may be easily worn to heal and close a plantar ulcer, and additionally, to maintain the plantar surface in a healed unulcerated state. Further, the '604 patent fails to disclose an orthosis, which may be easily donned and inserted inside a patient's modified street shoe.

U.S. Pat. No. 5,853,380 ('380 patent), which issued to Miller, discloses a Soft Ankle/Foot Orthosis. This invention comprises an upper portion and a lower portion formed of layers of soft material to surround the foot and lower portions of the leg. The layers of soft material thus form a split shell, which is sized and shaped to receive the lower leg and foot of a person desirous of orthotic treatment. One or more reinforcing stays are fixedly sandwiched between the inner layer and the outer layer to assist in holding the shell in its molded shape. The rigid reinforcing stay may be sandwiched between the layers of soft material in a generally L-shape to provide additional support to the leg and foot. A plurality of releasable fasteners is used to hold the shell in place on the wearer. It is further noted that the '380 patent does not disclose the use of a permanent orthosis, which may be easily worn to heal and close a plantar ulcer, and additionally, to maintain the plantar surface in a healed unulcerated state. Further, the '380 patent fails to disclose an orthosis, which may be easily donned and inserted inside a patient's modified street shoe.

U.S. Pat. No. 4,351,324 ('324 patent), which issued to Bronkhorst, discloses a Therapeutic Walking Device. This device is designed to reduce the tendency of persons with cerebral palsy to walk on the balls of their feet. The device comprises a foot section and a calf section formed at a 90-degree angle. The foot section has a heel support and a toe support, which supports are spaced so as to prevent pressure from being exerted on the sole of the foot between the heel and toes. The leg section is strapped about the calf of the user's leg. The '324 patent does not disclose the use of a permanent orthosis, which may be easily worn to heal and close a plantar ulcer, and additionally, to maintain the plantar surface in a healed unulcerated state. Further, the '324 patent fails to disclose an orthosis, which may be easily donned and inserted inside a patient's modified street shoe.

U.S. Pat. No. 3,916,886 ('886 patent), which issued to Rogers, discloses a Preformed Self-Conforming Drop Foot Brace. This brace comprises an upper calf portion and lower foot portion and is of such a structure that both the foot of the user and the lower portion of the brace maybe disposed in a shoe without alteration or modification of the latter. It is noted that due to the conforming nature of the brace, it is inconspicuous when worn for the upper portion of the brace may be situated within the confines of the trouser leg of a user, and the lower portion of the brace may be situated within a street shoe. The '886 patent, however, does not disclose the use of a permanent orthosis, which may be easily worn to heal and close a plantar ulcer, and additionally, maintain the plantar surface in a healed unulcerated state.

U.S. Pat. No. 5,571,077 ('077 patent), which issued to Klearman et al., discloses a Self-Supporting Foot Orthosis with Pivotally Mounted Cover. This invention comprises a generally L-shaped rigid shell for receiving a patient's lower leg and foot. The rigid shell further comprises a lower, correspondingly shaped rigid cover articulated at the rearmost portion of the upwardly extending part of the first shell. The cover may be pivoted downward, that is, away from the plantar portion of the first shell to provide a support that will elevate the patient's foot when the patient is lying down and which will cover the sole when it is pivoted toward the plantar portion of the foot. Apertures in the first shell allow the patient's foot to be treated and inspected when the cover is pivoted away from the plantar portion of the foot. The '077 patent does not disclose the use of a permanent orthosis, which may be easily worn to heal and close a plantar ulcer, and additionally, maintain the plantar surface in a healed unulcerated state. Further, the '077 patent fails to disclose an orthosis, which may be easily donned and inserted inside a patient's modified street shoe.

It will thus be seen from a review of the foregoing prior art references that the prior art thus perceives a need for a permanent orthosis, which may electively be worn throughout one's life, which may be easily donned and inserted inside a patient's modified street shoe. In this regard, it has been repeatedly shown that the cited patent disclosures do not disclose the use of a permanent orthosis, which may be easily worn to heal and close a plantar ulcer, and additionally, maintain the plantar surface in a healed, unulcerated state. Further, the cited prior art fails to disclose an orthosis for the treatment of plantar ulcers comprised primarily of vacuum form molded polypropylene or a similar polyester resin, which may be easily donned and inserted inside a patient's modified street shoe.

What is needed is a treatment device to aid in supporting the lower leg and foot of patients who have been diagnosed with diabetic neuropathic, Charcot joint and plantar ulcers with our without foot deformity. Current treatment modalities for plantar ulcers include reducing weight-bearing events through the use of crutches or total contact casts or wheelchairs. Additionally, surgical intervention is often employed. In this regard, it is noted that many ulcerated patients undergo surgery to remove the infected ulcer through partial foot amputation or to remove prominent bony areas that cause pressure problems. Typically, many of these patients will either develop plantar ulcers in a new area of the foot or the patient will refrain from walking so as to prevent any new ulcers. Often, after surgery, the patient's gait is affected due to missing bone structure in the foot region. None of the aforementioned remedies, however, offer a permanent solution to unloading or relieving pressure at the ulcer site.

SUMMARY OF THE INVENTION

Accordingly, it is an object of the present invention to provide an ankle/foot orthosis, which is custom-made for a patient suffering from plantar ulcer conditions and foot deformities for permanent or temporary use. It is a further object of the present invention to provide such an orthosis with unique construction, which construction provides an orthosis easily donned and worn in combination with a modified shoe for permanent or temporary use in standing or walking. It is a further object of the present invention to provide an orthosis, which allows for maximum support of a user's plantar foot surface. Still further, it is an object of the present invention to provide an effective treatment device for plantar ulcers, while stabilizing the ankle and plantar surface of the foot with attached custom alignment wedges, which provide balance and allow for a more normal gait. The present invention reduces pressure at the ulcer location and typically allows immediate ambulation upon its final fitting.

These and further objects are accomplished by the present invention which generally comprises a rigid, substantially L-shaped support member and a rigid anterior support shell hingedly articulated to the L-shaped support member. The L-shaped support member further comprises a substantially vertical, posterior support shell portion and a substantially horizontal, plantar support platform portion. The posterior support shell portion and plantar support platform portions are sized and shaped via state of the art casting and molding techniques to snugly receive the posterior portion of a user's lower leg and tarsal region, and the plantar portion of a user's foot. Proximally, the posterior support shell terminates in a proximal flared posterior shell brim. Distally, the posterior support shell terminates in a tarsal support structure, the tarsal support structure comprising a medial tarsal support portion, a lateral tarsal support portion, and a heel support portion intermediate the medial tarsal support portion and lateral support portion. Both the medial tarsal support portion and the lateral tarsal support portion extend in an anterior or ventral manner to a point intermediate the length of the plantar support platform. The orthosis is designed such that when a user dons the orthosis, the proximal flared posterior shell brim is located about ½ inch distally adjacent to the fibular head of the user's lower leg. The posterior support shell further comprises a circumferential corrugated rib structure intermediate the posterior support shell height for increasing the structural strength of the posterior support shell and to assist in guiding placement of an anterior support shell. The plantar support platform further comprises at least one ulcer-protecting hollow, which is spatially located for fitted placement in inferior adjacency to a user's diabetic plantar ulcer, thus allowing the user to transfer the user's weight away or off-load a user's weight from the plantar ulcer and facilitating plantar ulcer treatment.

The anterior support shell is designed for lateral hinged attachment to the posterior support shell and receives the anterior, proximal portion of a user's lower leg when the anterior support shell is hingedly closed and secured. The anterior support shell has a corresponding proximal flared anterior shell brim and a distal flared anterior shell brim. The anterior support shell is designed so that when a user is fitted with the orthosis, the proximal flared anterior shell brim is also spatially located for fitted placement in distal adjacency to the fibular head of the user leg. The anterior support shell further comprises a plurality of securing strap-receiving loops securely attached to the outer anterior support shell surface for receiving a plurality of securing straps.

A flexible, polyethylene hinge member hingedly attaches the anterior support shell to the posterior support shell. The hinge member allows the orthosis to be fully opened to receive a patient's leg and foot and then may be simply and securely fastened to the patient by closing and securing the anterior support shell. The hinge member hingedly attaches the anterior support shell to the posterior support shell such that the proximal flared anterior shell brim and flared posterior shell brim lie in substantially the same plane and such that the distal flared anterior shell brim and circumferential corrugated rib structure lie in substantially the same plane. The circumferential corrugated rib structure is designed to increase the structural strength of the posterior support shell and further for guiding placement of the anterior support shell.

Leg securement means, as preferably defined by a plurality of securing straps, are further disclosed. The securing straps each have an inner strap surface and an outer strap surface, where the outer strap surfaces further comprise hook and loop fastening means. The securing straps each have a posterior support shell attachment end and a securing strap feed end, which feed ends are fed through the securing strap receiving loops for securing the anterior support shell in fixed, weight-bearing relation about the proximal, anterior portion of the user's lower leg.

Additionally, posterior support shell padding may be attached to the inner posterior support shell surface for alleviating skin irritation of the posterior portion of a user's lower leg and tarsal region for maintaining total contact. In like manner, anterior support shell padding may be attached to the inner anterior support shell surface for alleviating skin irritation of the anterior, proximal portion of a user's lower leg for maintaining total contact and for relieving bony prominences. Further, plantar support platform padding may be attached to the plantar support platform for alleviating skin irritation of the plantar portion of a user's foot and for adjusting pressure points, as needed.

Once the configuration of the plantar portion of the orthosis is determined, the insole of a modifiable shoe customarily worn by the patient is ground out to conform to the contours of the plantar portion of the orthosis, thus allowing the patient to wear the shoe while avoiding undue pressure on portions of the plantar region having downwardly projecting bony prominences and ulcers.

BRIEF DESCRIPTION OF THE DRAWINGS

FIG. 8 is a perspective view of a clear synthetic plastic check socket for placement on a user's ulcerated foot.

FIG. 9 is a perspective view of a modified embodiment for the treatment of plantar or ulcers similar to FIG. 1 only illustrating a varied strap arrangement for attachment of the orthosis to a foot.

FIG. 16 illustrates a medial and lateral shells design of the orthotic device articulated at the ankle so as to provide ankle motion as prescribed by a doctor.

FIG. 17 illustrates a medial and lateral shells design wherein the medial and lateral shells terminate proximally to the ankle anatomical joint.

FIG. 18 illustrates another modified orthotic device where the ankle part of the support shell is rigid and is non-articulated.

FIG. 19 is a rear view of the orthotic device shown in FIG. 16.

FIG. 20 is a rear view of the orthotic device shown in FIG. 17.

FIG. 21 is a rear view of the orthotic device as shown in FIG. 18.

FIG. 22 is still another enlarged fragmentary modified form of a rigid orthotic device that fits into a modified boot or shoe with a foot being shown in broken lines relative thereto where a plantar distal edge extends to the toe and does not extend anteriorly or in a dorsal direction.

DETAILED DESCRIPTION OF THE PREFERRED EMBODIMENT(S)

Figure 1:
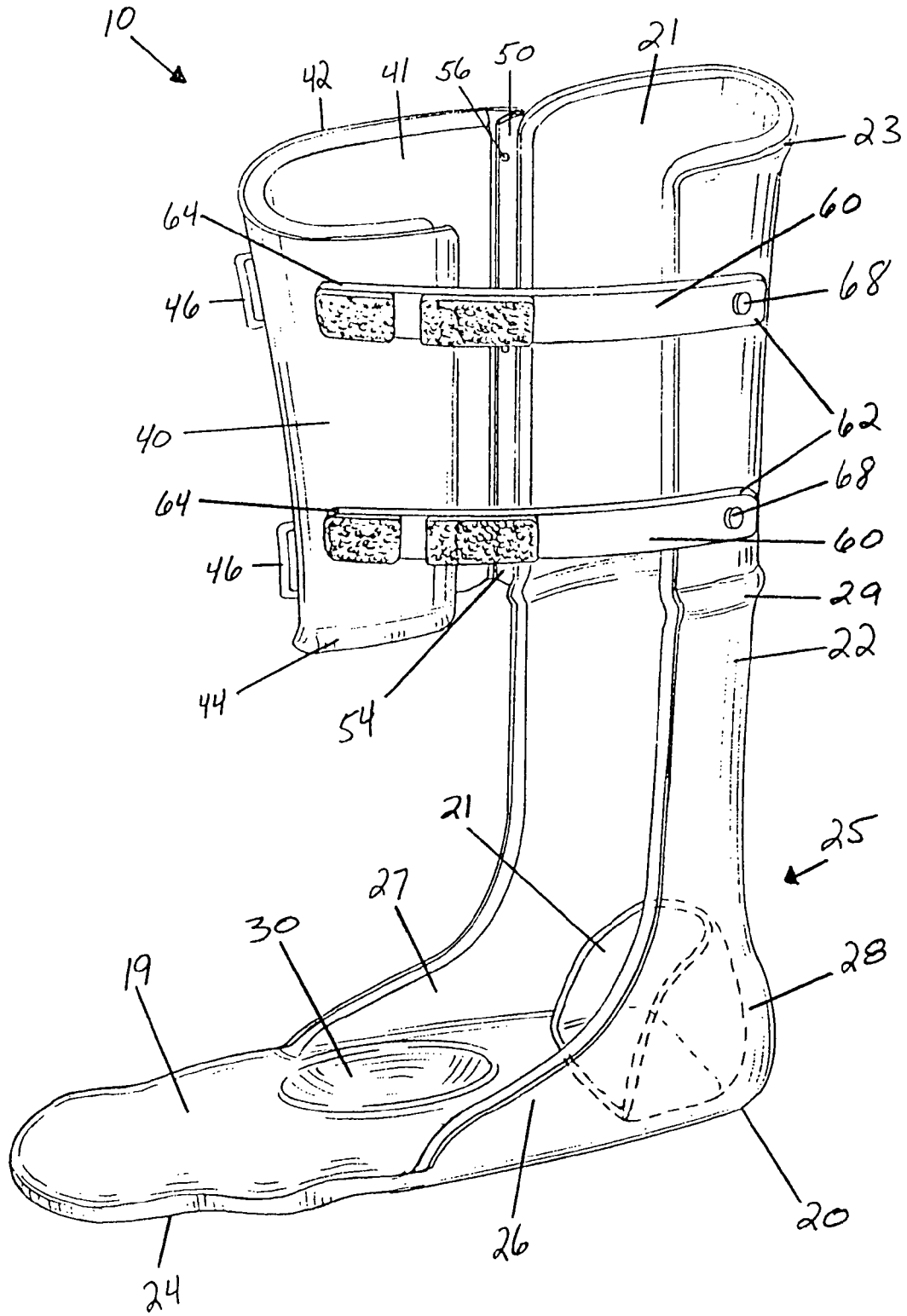
FIG. 1 is a perspective view of the preferred embodiment of the present invention showing the anterior support shell in an opened state for receiving a user's lower leg and foot.
Figure 2:
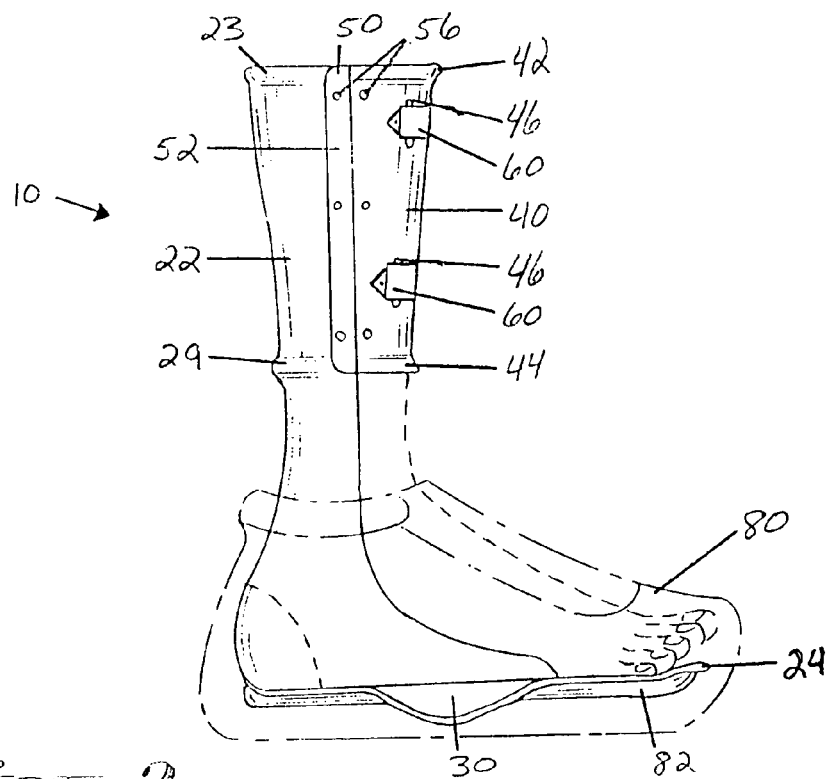
FIG. 2 is a right lateral view of a preferred embodiment of the present invention showing the invention applied to the right lower leg and foot of a user and showing, in partial sections, the positioning of the preferred embodiment within a shoe worn by the user.
Figure 14:
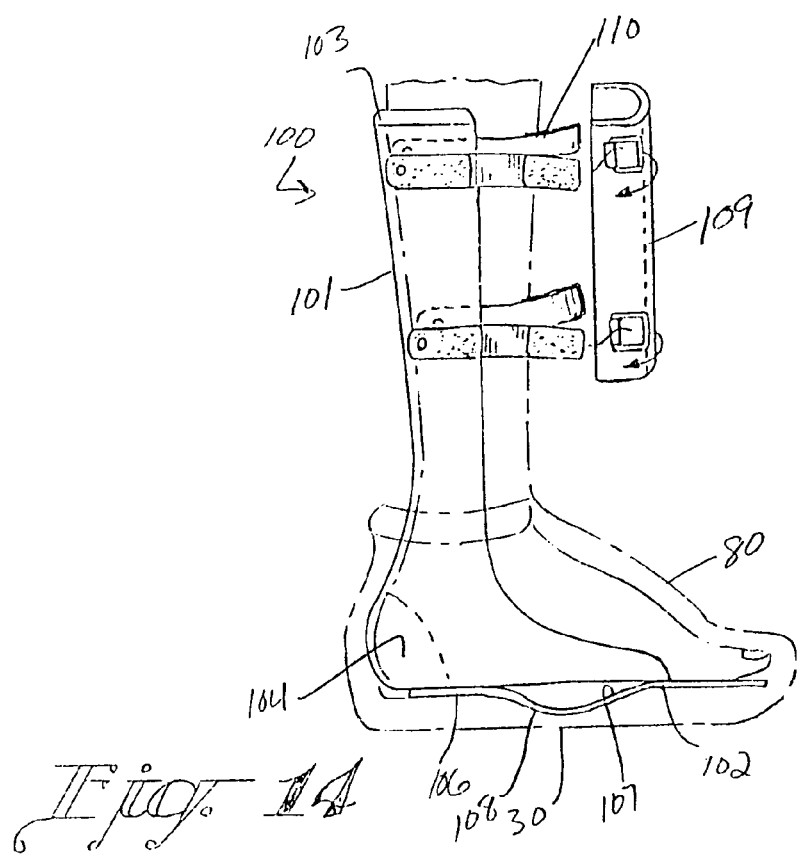
FIG. 14 is an exploded side view (shown in full and dotted lines) of still a further modification of my orthotic device similar to the one shown in FIG. 1 showing a completely removable anterior proximal section, wherein the anterior edges overlap the outside edge of the posterior section for securement with at least four straps outfitted with VELCRO brand hook and loop fastening means.

Referring now to the drawings, the preferred embodiment of the present invention, namely, a custom-made orthosis 10 for the treatment of diabetic plantar ulcers is generally illustrated and referenced in FIGS. 1-7. It is contemplated that custom-made orthosis 10 may be used in combination with a modified shoe 80 or other similar footwear for concealing custom-made orthosis 10 from general public view, as shown in FIGS. 2 and 14. In this regard, an orthotic system for treating plantar ulcers is contemplated, which system involves not only the fitting of custom-made orthosis 10 to the user, but also the insertion of custom-made orthosis 10 inside a modified shoe 80 or similar footwear. The orthotic system, or custom-made orthosis 10 used in combination with modified shoe 80, presents users with the option of utilizing an effective orthotic device without the social stigma often associated with readily apparent orthotic device use, as is often experienced with controlled ankle motion (CAM) walker usage. The contemplated orthotic system thus alleviates not only the user's plantar ulcer, but provides further relief from social stigmatization often associated with readily apparent orthotic device usage. In some cases, it should be noted that modified shoe 80 must be modified to accommodate custom-made orthosis 10, which modification is generally internal to modified shoe 80 and not readily apparent to passersby. Notably, the user may stand or walk while wearing the orthosis assembly.

Custom-made orthosis 10 is designed generally for supporting the lower leg and foot a user who has been diagnosed with diabetic, neuropathic, Charcot joint, plantar ulcers with or without foot deformity, or possibly blistered or callused portions of the user's foot. To this end, custom-made orthosis 10 generally comprises a rigid, substantially L-shaped support member 20 (as illustrated and referenced in FIGS. 1, 4 and 5) formed from state of the art casting and molding techniques. L-shaped support member 20 is preferably constructed from vacuum form molded polypropylene of about 3/16 inch thickness or a similar other polyester resin. It is noted that state of the art orthotics for the treatment of plantar ulcers have heretofore not been comprised of polypropylene and have not been constructed to be easily donned and inserted inside a modified street shoe. L-shaped support member 20 further comprises a substantially vertical, posterior support shell 22 (as shown in FIGS. 1, 2, 4, 5, 6 and 7) and a substantially horizontal, plantar support platform 24 (as shown in FIGS. 1, 2, 4, 5 and 6) formed as a continuous integral construction. Alternatively, it is contemplated that the posterior support shell or structure and the plantar support platform or structure can be constructed in separate portions. In this regard, it is contemplated that the plantar support portion or structure could conceivably be constructed from vacuum form molded polypropylene while the posterior support shell or leg support portion could be constructed from any number of suitable materials, including, but not limited to vacuum form molded polypropylene.

As shown, posterior support shell 22 has a posterior shell height, the dimension of which generally measures from the plantar region of the user's foot to a point distally adjacent to the fibular head region of the user's lower leg. As further shown, plantar support platform 24 has a platform length, the dimension of which generally measures from the posterior edge of a user's foot region to the anterior edge of the user's foot region. Posterior support shell 22 further comprises an inner posterior shell surface and an outer posterior shell surface. Posterior support shell 22 is sized and shaped to receive the posterior portion of a user's lower leg and tarsal region as shown in FIG. 2. As further shown in FIG. 2, plantar support platform 24 is sized and shaped to support the plantar portion of a user's foot.

Figure 3:
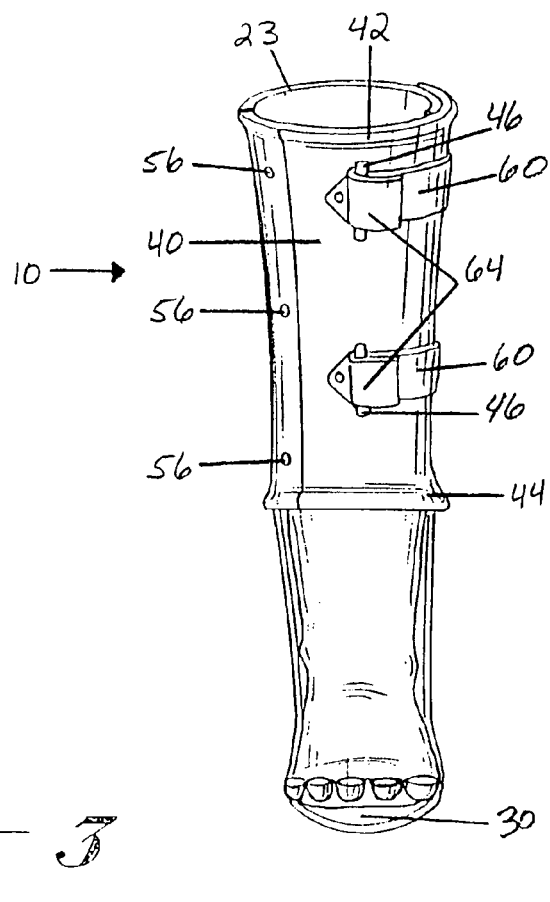
FIG. 3 is an anterior view of the preferred embodiment as attached to the right lower leg and foot of a user.
Figure 4:
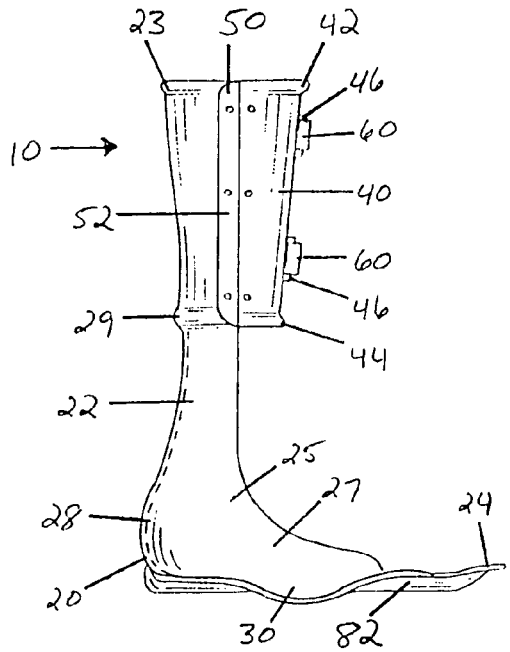
FIG. 4 is a right lateral view of a preferred embodiment in combination with a custom alignment wedge.
Figure 5:
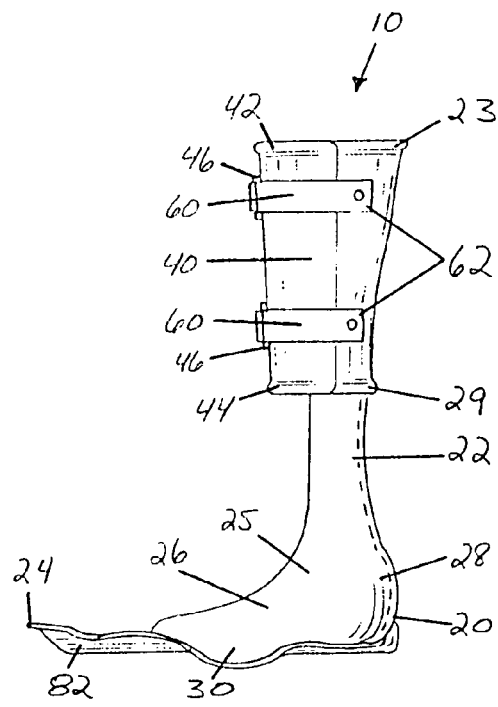
FIG. 5 is a right medial view of a preferred embodiment in combination with a custom alignment wedge.

The posterior support shell height terminates proximally in a proximal flared posterior shell brim 23 (as shown in FIGS. 1, 2, 3, 4, 5 and 7) and the posterior support shell height terminates distally in a tarsal support structure 25 (as shown in FIGS. 1, 4 and 5). Tarsal support structure 25 generally comprises a medial tarsal support portion 26 (as shown in FIGS. 1 and 5), a lateral tarsal support portion 27 (as shown in FIGS. 1 and 4), and a heel support portion 28 (as shown in FIGS. 1, 4 and 5) intermediate the medial tarsal support portion and lateral tarsal support portion. Medial tarsal support portion 26 and lateral tarsal support portion 27 provide added structural strength to the juncture of posterior support shell 22 and plantar support platform 24, and further provide rigid structural support for the tarsal region, which prevents ankle joint inversion and eversion and, further, prevents dorsiflexion and plantar flexion. Custom-made orthosis 10, thus, is not generally recommended for user's requiring ankle range of motion as part of a treatment regimen. However, the tarsal region may be modified to allow for range of motion, as prescribed. As shown, medial tarsal support portion 25 and lateral tarsal support portion 26 extend ventrally to a point intermediate the platform length. Proximal flared posterior shell brim 23 is spatially located for fitted placement in distal adjacency to the fibular head of a user's lower leg. Posterior support shell 22 further comprises a circumferential corrugated rib structure 29 (as shown in FIGS. 1, 2, 4, 5 and 7) intermediate the posterior support shell height for increasing the structural strength of posterior support shell 22 and for guiding placement of an anterior support shell, which structure is described below.

Plantar support platform 24 has a superior surface and an inferior surface and further comprises at least one ulcer-protecting hollow 30 as shown in FIGS. 1-7, and 9, 9(a), and 12-21. Further, plantar support platform is preferably contoured to conform to the patient's foot generally having a first anterior segment to support the patient's toes, a second anterior segment to support the metatarsal heads of the foot, an intermediate sole segment to support the arch of the foot and a posterior segment to support the heel of the foot. Ulcer-protecting hollow 30 is spatially located for fitted placement in inferior adjacency to a user's diabetic or other plantar ulcer. A typical location for ulcer-protecting hollow 30 is shown in FIG. 1, where plantar ulcers due to Charcot joint collapse are typically found approximately the mid-length of user's foot on the lateral half of the plantar area. Ulcer-protecting hollow 30 thus provides a rigid shield or rigid pocket to breathably receive the plantar ulcer at the superior surface of plantar support platform 24. Ulcer-protecting hollow 30 thus enables a user to transfer a user's weight away from the plantar ulcer when the inferior surface of plantar support platform 24 contacts stepping surfaces, thus facilitating plantar ulcer treatment, or the healing and closing (parenchymal regeneration) of an ulcerated site. When custom-made orthosis 10 is worn following ulcer closure, the prevention of further ulcers at the specific closed ulcer site is contemplated and achieved by ulcer-protecting hollow 30. As earlier stated, it is contemplated that the plantar support portion or structure could conceivably be constructed from vacuum form molded polypropylene. If so constructed, the off-loading, wound-protecting hollow 30 would then be molded into the material.

Custom-made orthosis 10 further preferably comprises a rigid, anterior support shell 40 as shown in FIGS. 1-6, inclusive and as referred to above. Anterior support shell 40 is preferably designed for lateral hinged attachment to posterior support shell 22 and provides custom-made orthosis 10 with a rigid, weight-bearing area. In this regard, a lateral hinge attachment is to be preferred, since the medial tibial flare of the user's lower leg is typically a weight-bearing portion of the user's lower leg and medial closing securement reinforces this weight-bearing characteristic. The preferred lateral hinge attachment advantageously incorporates the natural form and function of the medial tibial flare into its preferred design. Anterior support shell 40 is preferably comprised of drape molded 3/16 inch polyethylene or similar polyester resin and has an inner anterior support shell surface and an outer anterior support shell surface. Anterior support shell 40 is designed to receive the anterior, proximal portion of a user's lower leg.

Anterior support shell 40 has a proximal flared anterior shell brim 42 (as shown in FIGS. 1-6, inclusive) and a distal flared anterior shell brim 44 (as shown in FIGS. 1-6, inclusive). Proximal flared anterior shell brim 42 is spatially located for fitted placement in distal adjacency to the fibular head of the user's leg. Anterior support shell 40 further comprises securing strap receiving structure, which preferably further comprises a plurality of securing strap receiving loops 46 (as shown in FIG. 1-6, inclusive) securely attached to the outer anterior support shell surface. Securing strap-receiving loops 46 preferably comprise 2-inch metal buckle loop retainers. Receiving loops are preferably attached the outer surface of anterior support shell 40 using plastic chafe structures, which chafe structures are preferably riveted to the outer surface of anterior support shell 40, substantially as shown.

Figure 6:
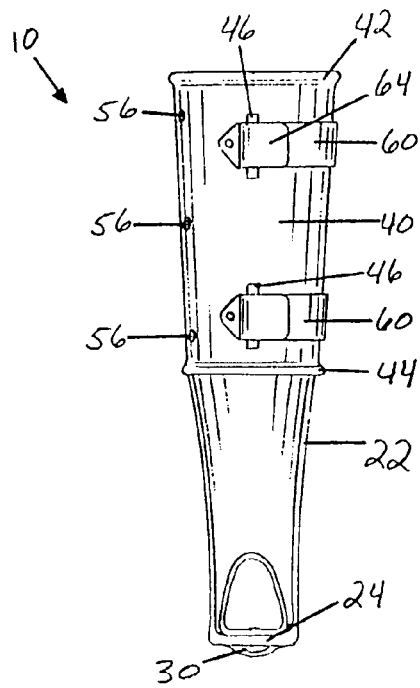
FIG. 6 is an anterior view of a preferred embodiment.
Figure 7:
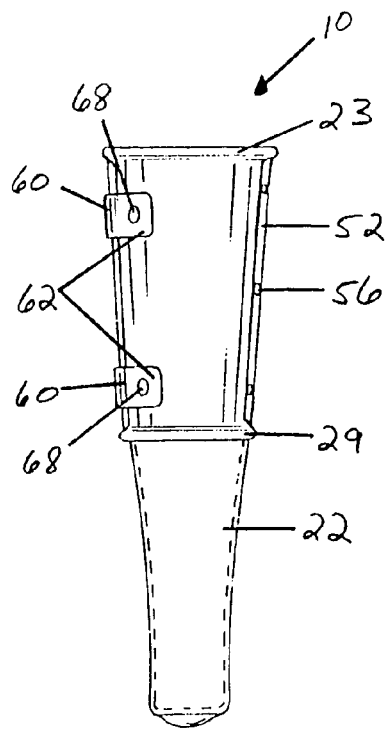
FIG. 7 is a posterior view of the preferred embodiment shown in FIG. 6.

Custom-made orthosis 10 further preferably comprises hinge means for hingedly attaching anterior support shell 40 to posterior support shell 22. Preferably, the hinge means is further defined by comprising a flexible polyethylene hinge member 50 (as shown in FIGS. 1, 2 and 4) for hingedly attaching anterior support shell 40 to posterior support shell 22. Hinge member 50 has an inner hinge surface, an outer hinge surface, and preferably, a hinge member thickness of about 1/16 inch. Hinge member 50 further has a posterior hinge portion 52 as shown in FIGS. 2, 4 and 7, and an anterior hinge portion 54 as shown in FIG. 1. The outer hinge surface of anterior hinge portion 52 is preferably securely fastened to the lateral most edge of the inner anterior support shell surface and the inner hinge surface of posterior hinge portion 54 is securely fastened to the lateral most edge of the outer posterior support shell surface. Preferably, copper rivets 56 (as shown in FIGS. 1, 2, 3, 4, 6 and 7) fasten hinge member 50 to anterior support shell 40 and posterior support shell 22. Excellent results have been found when SPEEDY brand rivets 56 are used in the installation of hinge member 50 as described. Hinge member 50 thus hingedly attaches anterior support shell 40 to posterior support shell 22 such that proximal flared anterior shell brim 42 and proximal flared posterior shell brim 23 lie in substantially the same plane and further such that distal flared anterior shell brim 44 and circumferential corrugated rib structure 29 lie in substantially the same plane.

In this last regard, it is noteworthy that circumferential corrugated rib structure 29 is preferably located at the distal calf muscle area. Not only does circumferential corrugated rib structure 29 add strength to posterior support shell 22, but further provides guiding placement of distal flared anterior support shell brim 44 of anterior support shell 40 .as shown in FIGS. 2, 4 and 5. Further, the plane in which the flared proximally-located shell brim structures lay is preferably located distally about ½ inch from the fibular head of the user's lower leg. Hinge member 50 further acts as a placement for anterior support shell 40 to prevent anterior support shell 40 from moving proximally or distally, which movement would throw off the actual alignment of the weight-bearing areas.

Custom-made orthosis 10 further comprises securing means for securing anterior support shell 40 to posterior support shell 22 in fixed, weight-bearing relation about the anterior, proximal portion of a user's leg. In this regard, the securing means is defined by preferably comprising a plurality of securing straps 60 as shown in FIGS. 1-7, inclusive, which straps are preferably 2 inches in width. Securing strap length is dependent upon the needs of the individual user. Securing straps 60 each have an inner strap surface comprised primarily of nylon webbing and an outer strap surface. The outer strap surface is preferably comprised of hook and loop fastening means, which may be defined by preferably comprising VELCRO brand hook and loop structure. Securing straps 60 each further have a posterior support shell attachment end 62 as shown in FIGS. 1, 5 and 7 and a securing strap feed end 64 as shown in FIGS. 1, 3 and 6. Posterior support shell attachment ends 62 are securely fastened to the medial portion of posterior support shell 22. Preferably, posterior support shell attachment ends 62 are fastened to posterior support shell 22 by rivets 68, preferably comprised of copper. Excellent results have been achieved by using SPEEDY brand rivets 68 to secure posterior support shell attachment ends 62 to posterior support shell 22 in that installation is fast and easy. To secure anterior support shell 40 about the user's leg, securing strap feed ends 64 are each fed through securing strap receiving loops 46 and doubled back upon themselves for securing anterior support shell 40 in fixed, weight-bearing relation about the anterior, proximal portion of the user's lower leg. When anterior support shell 40 is secured about the anterior, proximal portion of the user's lower leg, the medial most edge of anterior support shell 40 preferably overlaps the medial most edge of posterior support shell 22 preferably about ¾ inch as shown in FIG. 3.

The leg securement means or connecting means join the inner strap surface and the outer strap surface in secured manual detachable engagement, the securing straps each having a posterior shell attachment end fixedly attached to the anterior support shell for fixed weight bearing engagement about the anterior portions of the user's lower leg.

Custom-made orthosis 10 further preferably comprises posterior support shell padding 21 as shown in FIG. 1, which may be attached to the inner posterior support shell surface for alleviating skin irritation of the posterior portion of a user's lower leg and tarsal region and for maintaining total contact between a user's lower leg and the fitted orthosis. In this regard, it is contemplated that posterior support shell padding 21 may be typically attached to the inner posterior shell surface at proximal portions of posterior support shell 22 to alleviate frictional forces and sheer, and at the heel support portion of the tarsal support region to alleviate heel pumping and the resultant excessive skin irritation. It is to be further understood that when rivets 56 securely fasten the inner hinge surface of posterior hinge portion 54 to the lateral most edge of the outer posterior support shell surface, rivets 56 are hidden from view by being sandwiched between the inner posterior support shell surface and posterior support shell padding 21. Preferably, posterior support shell padding 21 comprises closed cell polyurethane padding.

Custom-made orthosis 10 further preferably comprises anterior support shell padding 41 as shown in FIG. 1, which is attached to the inner anterior support shell surface for generally preventing frictional forces and sheer, thus alleviating skin irritation of the anterior, proximal portion of a user's lower leg as well as for maintaining total contact. Anterior support shell padding 41 further provides bony relief. Preferably, anterior support shell padding 41 comprises closed cell polyurethane padding. Custom-made orthosis 10 further preferably comprises plantar support platform padding 19, which is attached to plantar support platform 24 for alleviating skin irritation of the plantar portion of a user's foot and for adjusting pressure points, as needed. Plantar support platform padding 19 preferably comprises a ⅛ inch or less closed cell polyurethane padding. Plantar support platform padding 19 may further comprise a raised arch portion, as required by the user.

It is noted that, given the state of the art, an orthosis comprised of polypropylene or a similar polyester resin for the treatment of plantar ulcers would not be recommended for use on a diabetic patient for the treatment of plantar ulcers. This is due to the current understanding in the prior art literature that polypropylene orthoses could cause sheering and skin breakdown of the diabetic patient thus creating a new pressure sore or decubitus ulcer on a user's leg. The present invention is comprised almost entirely of plastic as described. The exceptions to the materials composition are primarily the padded areas to help in applying or having weight distributed across the anterior support shell and plantar support platform of the foot region. Additionally, common art bladders may be used in conjunction with posterior support shell padding 21 to accommodate leg size variance within a given user. The present invention thus overcomes the state of the art insofar as a custom-made orthotic for use in the treatment of plantar ulcers is provided, which orthotic is comprised primarily of polypropylene plastic. Further, the described orthotic may easily be donned and worn inside of a modified shoe with typical internal modification.

Figures 9A, 10:
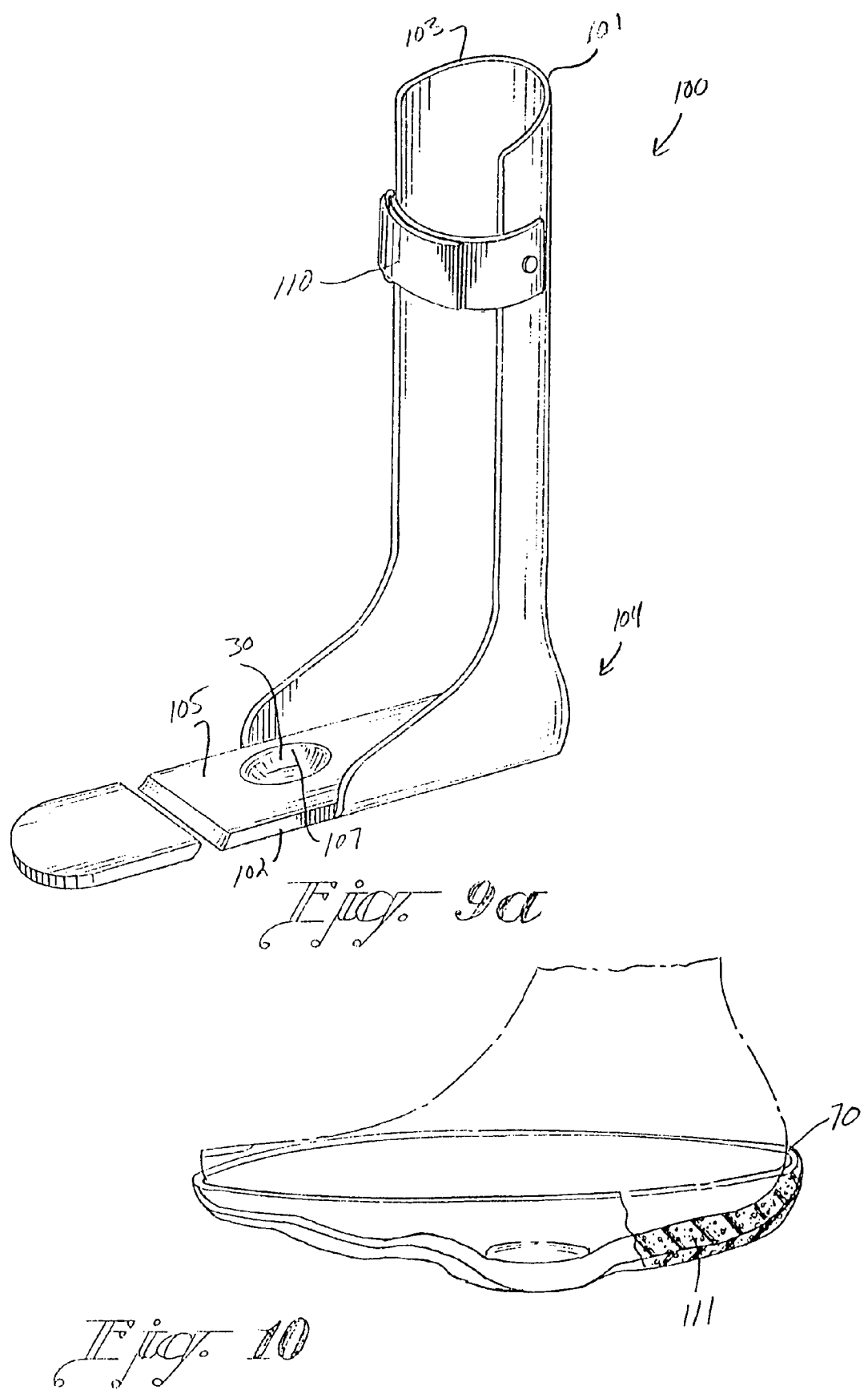
FIG. 9(a) is a perspective view of still a further modification showing how the orthosis in FIG. 9 can be reduced in length for securement to the foot of an amputee where part of the foot has been amputated.
FIG. 10 is a fragmentary view of a soft orthotic device with padding having been added and illustrated with portions of the orthotic device broken away for illustrative purposes with a foot being shown as mounted on the orthotic device and as illustrated by the dotted lines.

Custom-made orthosis 10 is generally formed through common art practices where a cast is taken of the user's lower leg and foot, which cast is then removed from the user's lower leg and foot and filled in a typical fashion with a plaster liquid. The plaster liquid is then allowed to harden, leaving a replica or positive model of the user's foot and leg. At some-point before the formation of L-shaped support member 20, a further inventive step involves the formation of a clear plastic check socket 70 from the positive model, which check socket 70 is shown in FIGS. 8, 10, and 22. Check socket 70 typically resembles plantar support platform 24 structurally, but is a preliminary form for plantar support platform 24. As indicated, check socket 70 is preferably comprised of a clear plastic and is then fitted to the plantar portion of a user's foot, which provides the manufacturer of custom-made orthosis 10 with a visual opportunity to make a detailed inspection of the plantar portion of a user's foot. Noting problematic portions of the check socket in relation to the positive model, particularly with regard to the weight-bearing areas of L-shaped support member 20, the manufacturer of custom-made orthosis 10 may more easily make modifications to the positive model before L-shaped support member 20 is finally formed. Custom-made orthosis 10 may be more confidently vacuum molded following the indicated check socket procedure to provide a more effective orthosis.

L-shaped support member 20 is typically molded first, and trimmed as needed. Anterior support shell 40 is typically molded after L-shaped support member and trimmed as needed. Once custom-made orthosis 10 is constructed as described, it may then be fitted into modified shoe 80 by grinding out an ulcer-protecting hollow receiving structure in the shoe insole to accommodate ulcer-protecting hollow 30. When custom-made orthosis 10 is to be utilized, the user may hingedly operate anterior support shell 40 to an open position. Thereafter, the user may position the user's foot with the user's heel in heel support portion 28 and with the user's plantar ulcer site 90 (as diagrammatically shown in FIG. 8) positioned at ulcer-protecting hollow 30. Again, it should be noted that it is contemplated that the foot support portion of the orthotic assembly may thus be formed or constructed from vacuum form molded polypropylene, the off-loading, wound-protecting hollow 30 being molded into the material.

Anterior support shell 40 is then secured to a user's lower leg by threading securing straps 60 through securing strap receiving loops 46 by pulling securing straps 60 taught and fastening securing straps 60 to themselves through the use of the hook and loop fastening means located on the outer strap surface of securing straps 60. The user may then insert the user's foot along with custom-made orthosis 10 into modified shoe 80 aligning ulcer-protecting hollow 30 into modified shoe 80, thus effectively receiving custom-made orthosis 10 and the user's foot. It is further contemplated that expedients such as wedges 82, for example, heel or sole wedges, lateral or medial or both, may be attached in distal adjacency to the inferior surface of plantar support platform 24 to provide additional stability to custom-made orthosis 10 as shown in FIGS. 2, 4 and 5. An exemplary wedge 82 is shown in FIGS. 2, 4 and 5.

The reader will thus see that it is an object of the present invention to provide an ankle/foot orthosis, which may be custom-made for a patient suffering from plantar ulcer conditions for permanent use. It will be further seen that an object of the present invention to provide such an orthosis with unique construction, which construction provides an orthosis easily donned and worn in combination with a modified shoe. Still further, it will be seen that an object of the present invention to provide an orthosis, which allows for maximum support of a user's plantar foot surface. Yet further, it will be seen that the present invention provides an effective treatment device for plantar ulcers, while stabilizing the ankle and plantar surface of the foot with attached custom alignment wedges, which provide balance and allow for a more normal gait. The present invention reduces pressure at the ulcer location and typically allows immediate ambulation upon its final fitting.

It is contemplated that the orthosis for the treatment of plantar ulcers and foot deformities herein illustrated and described is used primarily for descriptive and illustrative purposes and should not be construed to limit the scope of concept application to the application as shown. For example, it is contemplated that the hinge means need not comprise a flexible polyethylene hinge member. So long as functional, unobtrusive hinge means hingedly attach anterior support shell 40 to posterior support shell 22, the primary objectives of the present invention may still be achieved. In this regard, hinge means comprising a flexible polyethylene hinge member preferably fulfills this function.

Further, it is contemplated that securing means for securing anterior support shell 40 in fixed, weight-bearing relation about the proximal portion of a user's lower leg need not comprise securing straps as described herein. So long as functional, unobtrusive securing means secure anterior support shell 40 in fixed, weight-bearing relation about the proximal portion of a user's lower leg, the primary objectives of the present invention may still be achieved. In this regard, securing means comprising securing straps in combination with securing straps receiving loops preferably fulfills this function.

Notably, if reduced edema or healing of the ulcer or wound occurs, an alternative orthotic design may be necessary as prescribed by appropriate caretakers. Thus, it is further contemplated that the orthosis assembly may be replaced by an alternative orthotic design as prescribed given a select biological development, the select biological development being selected from the group consisting of reduced edema and ulcer healing.

It is contemplated that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures herein performing the recited functions and not only structural equivalents, but equivalent structures as well. For the purposes of the present disclosure, two structures that perform the same function within an environment described above may be equivalent structures.

Alternative Embodiment(s)

Having thus specified the preferred embodiment(s), it should be noted that a number of alternative embodiments are contemplated, as described in more detail hereinafter. Notably, a clear check socket fitting is required prior to constructing any of the following alternative embodiments. From an inspection of FIG. 9, it will be seen that the present invention contemplates an orthosis assembly for the treatment of diabetic plantar ulcers wherein the orthosis assembly comprises a substantially L-shaped lower leg support structure (such as L-shaped support member 20) as generically referenced at 100 in FIGS. 9, 9(a), 11(a)-14, and 16-18; and leg securement means 110 as generically illustrated and referenced in FIGS. 9, 9(a), and 11(a)-21.

The lower leg support structure comprises at least one substantially vertical, leg support portion 101 as generically illustrated and referenced in FIGS. 9, 9(a), and 11(a)-21; and a substantially horizontal, foot support portion 102 as further generically illustrated and referenced in FIGS. 9, 9(a), and 11(a)-22. The leg support portion 101 and the foot support portion 102 may preferably be constructed by way of a state of the art or commonly used lamination process, the lamination process utilizing a select resin, the select resin being selected from the group consisting of polyester resin and acrylic resin. Alternatively, the foot support portion 102 may be constructed from vacuum form molded polypropylene, the off-loading, wound-protecting hollow 30 being molded into the material.

Figure 11A:
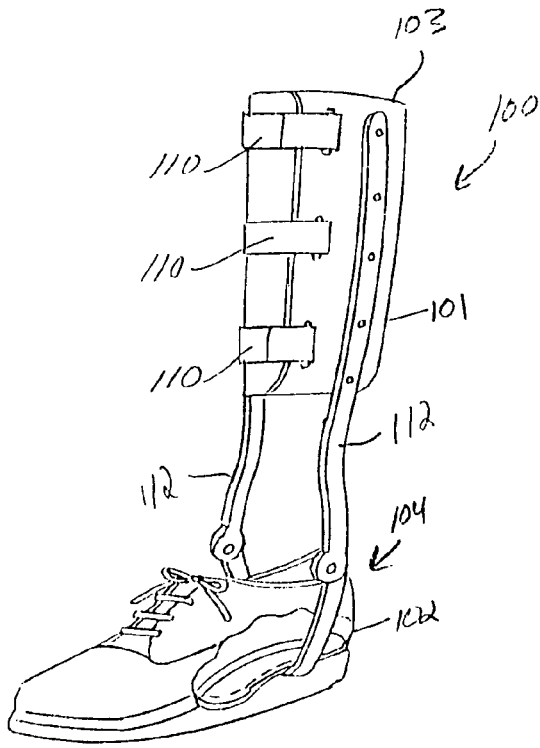
FIG. 11(a) is a further modified orthotic device shown in combination with a shoe and a leather calf structure held in place by metal uprights to provide solid or adjustable ankle joints, as required by using "Velcro" closure straps.
Figure 11B:
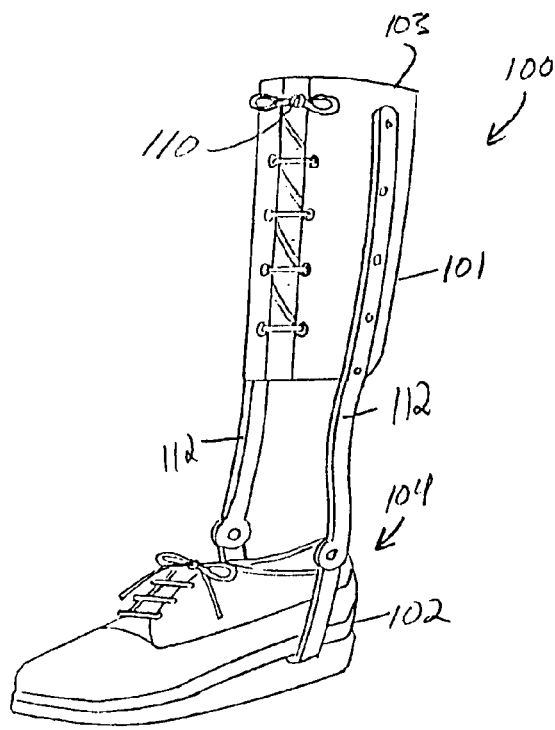
FIG. 11(b) is a view similar to the one shown in FIG. 11a only with eyelets and shoe laces having been substituted for the "Velcro" closure straps.
Figure 12:
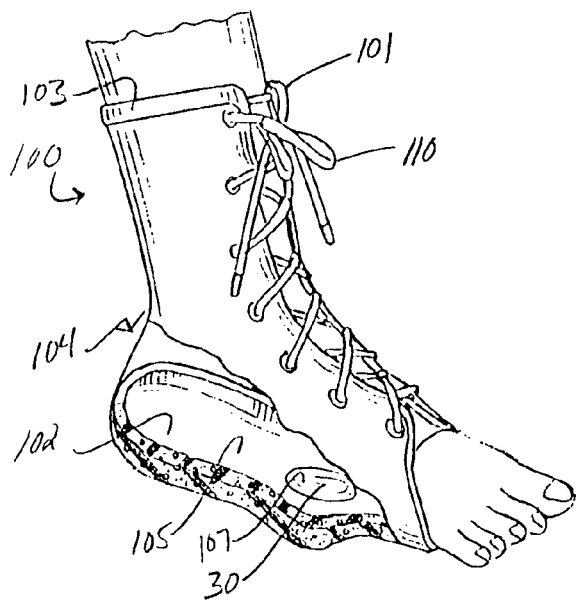
FIG. 12 illustrates still another modification where an orthotic device similar to the one illustrated in FIG. 10 is mounted inside of a modified boot or shoe and where certain parts are broken away to show the positioning of my orthotic device internally of the modified boot or shoe to give greater support to the ankle and foot.
Figure 15:
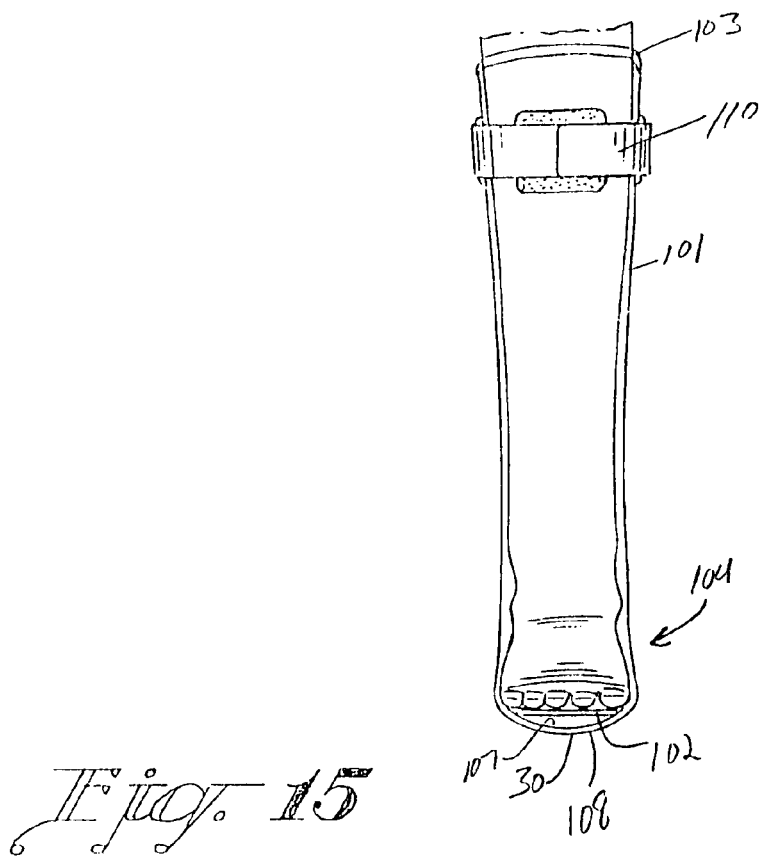
FIG. 15 is an anterior view of the orthotic device shown in FIG. 9.

It will be readily understood that the leg support portion 101 is preferably sized and shaped to receive a portion of a user's lower leg (whether proximal or distal relative to the knee region) and the foot support portion 102 is preferably sized and shaped to support a portion of a user's foot as generally depicted in FIGS. 12, 14, and 15. The leg support portion 101 terminates proximally in an upper rim 103 as generically depicted in FIGS. 9, 9(a), and 11(a)-21; and terminates distally in a tarsal support structure 104 as generically depicted in FIGS. 9, 9(a), and 11(a)-21. From an inspection of FIGS. 9, 9(a), 11(a), 11(b), 13, 15, and 19-21, it will be seen that the tarsal support structure 104 preferably comprises a medial tarsal support portion and a lateral tarsal support portion, the medial tarsal support portion and the lateral tarsal support portion being cooperatively associated with the foot support portion 102.

The upper rim 103 is spatially located for fitted placement distal to the knee region of a user's lower leg. The foot support portion 102 inherently has a superior foot support surface 105 as referenced in FIGS. 9, 9(a), 10, 12, 13, and 22; an inferior foot support surface 106 as referenced in FIGS. 10, 14, and 22; and at least one rigid, weight-bearing, wound-protecting hollow 30. Notably, hollow 30 inherently has a superior hollow surface 107 as referenced in FIGS. 9, 9(a), 12, 14, and 15; an inferior hollow surface 108 as referenced in FIGS. 14 and 15. It will be understood from an inspection of the noted figures that the superior hollow surface 107 is continuous with the superior foot support surface 105 and the inferior hollow surface 108 is continuous with the inferior foot support surface 106. It will be further recalled that hollow 30 is designed for fitted placement in inferior adjacency to a user's diabetic plantar ulcer or similar other plantar wound. In this regard, the superior hollow surface 107 is preferably spaced from the user's diabetic plantar ulcer or plantar wound so as to promote healing thereof. Ulcer-protecting hollow or wound-protecting hollow 30 thus enables a user to transfer a user's weight away from the plantar ulcer or plantar wound when the inferior surface of the foot support portion 102 contacts stepping surfaces, thus facilitating plantar wound treatment, or the healing and closing (parenchymal regeneration) of an ulcerated site. When custom-made orthosis 10 is worn following ulcer closure, the prevention of further ulcers at the specific closed ulcer site is contemplated and achieved by ulcer-protecting hollow 30.

Figure 13:
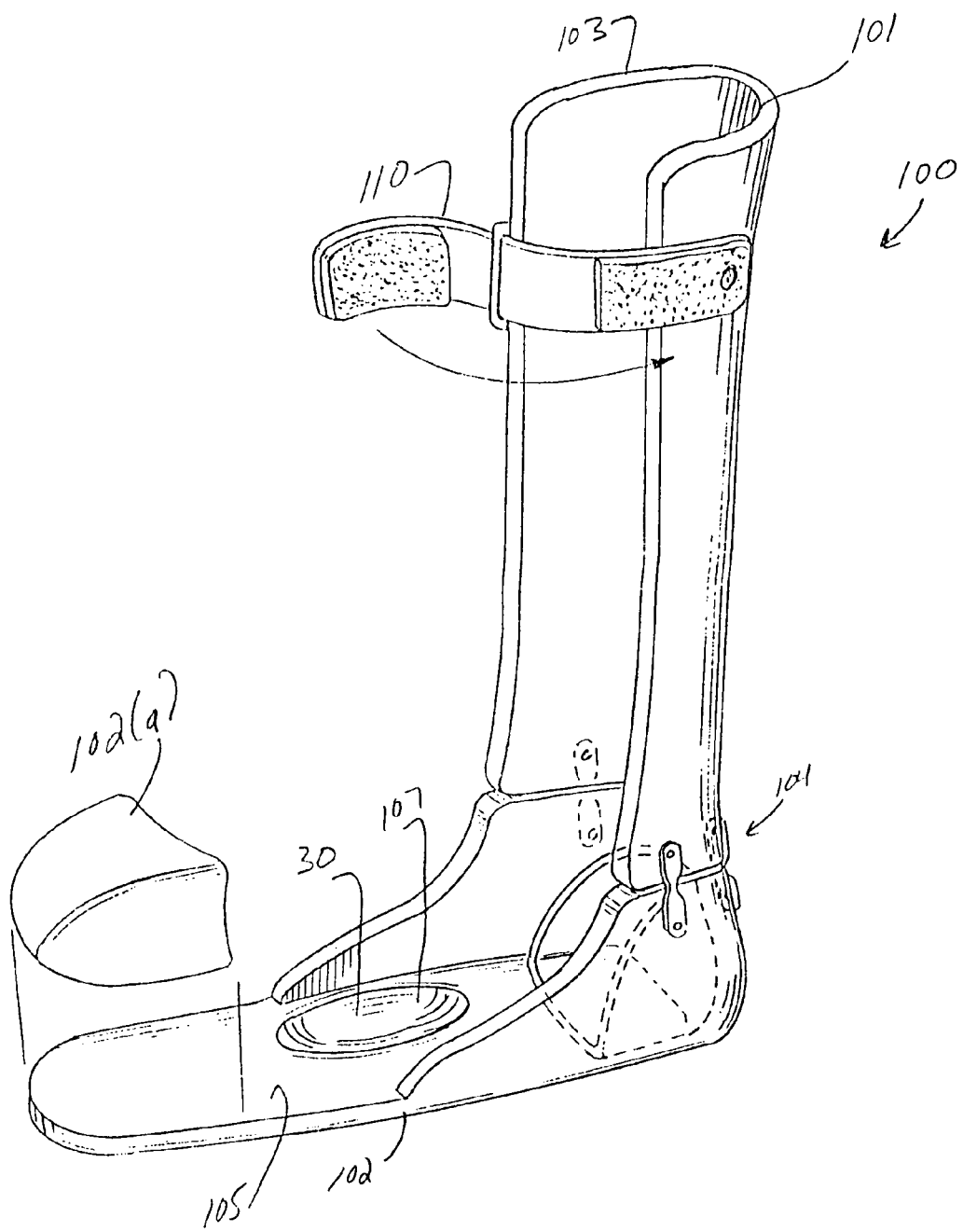
FIG. 13 illustrates a still further modification of my orthotic device similar to the one shown in FIG. 9 with an optional section being removable where the orthotic device is to be used by an amputee with part of a foot having been amputated and with a calf section being secured to my orthotic device by fasteners and with a hook on the parts as also illustrated in FIG. 1.

The leg securement means are designed to as to selectively encircle the user's lower leg for securing the leg support portion 101 to the user's lower leg. FIG. 9, for example, is a perspective view of a modified embodiment for the treatment of plantar or ulcers similar to what is shown in FIG. 1 only illustrating varied leg securement means (i.e. a first varied strap arrangement or tie member arrangement) for attachment of the orthosis to a user's lower leg. FIGS. 13 and 15 are alternative views of the assembly wherein the first varied strap arrangement is illustrated. FIGS. 11(a) depicts a second varied strap arrangement (three leg-encircling straps); FIG. 14 depicts a third varied strap arrangement (two pairs of cooperatively associated straps in combination with an anterior leg support portion 109); and FIGS. 16-21 depict a series of fourth strap arrangements (two leg encircling straps). Notably, the anterior leg support portion 109 or anterior portion of the leg support portion 101 is removably attachable to the leg support portion 101 and is preferably constructed from 3/16 polyethelene thermo form plastic. Further, FIGS. 11(b) and 12 depict an eyelet and lacing assembly for securing the orthotic assembly to the user's lower leg. The eyelet and lacing assemblages or tie members have been substituted for the "Velcro" type closure straps as otherwise depicted.

FIG. 9(a) depicts how the orthosis in FIG. 9 can be reduced in length for securement to the foot of an amputee where part of the foot has been amputated. In FIG. 10, a fragmentary view of a modified orthotic device similar to the one shown in FIG. 8 is shown. The FIG. 10 device illustrates the device shown in FIG. 8 with the exception that FIG. 10 depicts added padding 111. It will be seen from an inspection of FIG. 10 that certain portions of the orthotic device have been broken away for illustrative purposes with a foot being shown as mounted on the orthotic device as illustrated by broken lines.

FIG. 10 is a fragmentary view of a soft orthotic design with padding having been added and illustrated with portions of the orthotic device broken away for illustrative purposes with a foot being shown as mounted on the orthotic device and as illustrated by the dotted lines. In other words, FIG. 10 is a cutaway view of multiple layers of select densities of foam padding. It is contemplated that the foot support portion of the orthotic assembly may thus be formed or constructed from vacuum form molded polypropylene, the off-loading, wound-protecting hollow 30 being molded into the material.

FIG. 11(a) depicts a further modified orthotic device shown in combination with a shoe and a leather calf structure held in place by metal uprights to provide solid or adjustable ankle joints, as required by using "Velcro" closure straps. FIG. 12 depicts still another modification where an orthotic device that is designed to be mounted or worn inside of a modified boot or shoe. FIG. 12 depicts the structure with certain parts broken away to show the positioning of the hollow 30 relative to user's foot and to further illustrate a lower leg support structure constructed from materials that may be easily donned for fitted placement inside a modified boot or shoe to give greater support to the ankle and foot. FIG. 13 depicts a lower leg support structure 100 with an optional section being removable as depicted at referenced numeral 102(a). In this regard, it is contemplated that the orthotic device may be used by an amputee with part of a foot having been amputated and with the leg support portion being secured to the user's leg with straps outfitted with hook and loop fastening means. In this last regard, it will be understood that the present invention contemplates an orthosis assembly wherein the foot support portion comprises a plurality of regions or a region grouping, the region grouping comprising a partial foot filler prosthesis as referenced at 102(a) in FIG. 13. The partial foot filler prosthesis 102(a) is designed for filling space adjacent the user's foot, the user's foot having been amputated at a point intermediate the toe region and heel region.

The orthosis assembly further contemplates a lower leg support structure comprising select ankle support means, the select ankle support means being selected from the group consisting of ankle movement-enabling means (e.g. an articulated ankle structure) and ankle movement-restricting means (e.g. a rigid ankle housing). The orthosis assembly further contemplates select orthotic accessories, the select orthotic accessories being selected from the group consisting of at least one rigid upright assembly and at least one modified shoe. The rigid upright assembly (e.g. two metal upright members referenced at 112 in FIGS. 11(a) and 11(b)) is cooperatively associated with the leg support portion 101 and the foot support portion 102 for providing select support reinforcing means. The select support reinforcing means are selected from the group consisting of ankle movement-enhancing means (e.g. articulated metal upright members) and ankle movement-preventing means (non-articulated metal upright members).

More particularly, the present invention discloses an orthosis assembly for the treatment of plantar wounds, the orthosis assembly comprising a rigid, substantially L-shaped support member, a first securing strap 120, and a second securing strap 121 as illustrated and referenced in FIGS. 9 and 9(a). The L-shaped support member comprises a substantially vertical, posterior support shell 122 and a substantially horizontal, plantar support platform 123 as further referenced in FIGS. 9, 9(a), 13, and 14. The posterior support shell 122 comprises an inner posterior shell surface 124, an outer posterior shell surface 125, a first posterior shell edge 126, and a second posterior shell edge 127 as illustrated and referenced in FIGS. 9, 9(a), and 13. It will be noted from an inspection of the noted figures that the second posterior shell edge 127 is laterally opposite the first posterior shell edge 126.

The posterior support shell 122 is sized and shaped to receive the posterior portion of a user's lower leg and the plantar support platform 123 is sized and shaped to support the plantar portion of a user's foot. The plantar support platform 123 comprises a superior platform surface 128 and an inferior platform surface 129 as illustrated and referenced in FIGS. 9, 9(a), 13, and 14, and at least one rigid, weight-bearing or off-loading ulcer or wound-protecting hollow 30 as previously specified. It is contemplated that if the orthotic assembly is to be used without the use of a modified shoe, the orthotic assembly could conceivably be utilized in combination with a sole, the sole being adhesively attached to the inferior platform surface 129 (not specifically illustrated), the adhesively attached sole enabling the user to safely ambulate without a shoe.

The first and second securing straps 120 and 121 each comprise an inner strap surface, an outer strap surface, a shell attachment end, and a strap engagement end. The shell attachment ends are fixedly secured to the first and second posterior shell edges 126 and 127 as may be seen from an general inspection of the noted figures. The inner strap surface of the first securing strap comprises first strap fastening means and the outer strap surface of the second securing strap comprising second strap fastening means, the first and second strap fastening means being cooperatively associated and fastenable about the user's lower leg for securing the posterior support shell 122 to the user's lower leg. Preferably, the first and second strap fastening means are defined by VELCRO brand matable hook and loop fastening means.

The plantar support platform 123 inherently comprises a platform length, the length of which may be abbreviated (as generally depicted or referenced at 130 in FIG. 9(a)) for supporting a user's partially amputated foot. Further, it is contemplated that the present invention may comprise a partial foot filler prosthesis 102(a). The orthosis assembly may further comprise support fastening means 131 as illustrated and referenced in FIG. 13. In this regard, it will be noted that the posterior support shell 122 may be separable from the plantar support platform 123, the support fastening means 131 fastening the posterior support shell 122 to the plantar support platform 123.

Alternatively, the present invention contemplates an orthosis assembly for the treatment of plantar wounds comprising an L-shaped support member and at least one securing strap 133 as illustrated and referenced in FIG. 13. The L-shaped support member comprises a posterior support shell 122 wherein at least one strap-securing loop 132 is affixed to either the first posterior shell edge 126 or the second posterior shell edge 127 as illustrated and referenced in FIG. 13. In this regard, it will be noted that the strap-securing loop 132 is fixedly attached to a select shell edge, the select shell edge being selected from the group consisting of the first and second posterior shell edges 126 and 127. Further, the securing strap comprises an inner strap surface (not specifically referenced), an outer strap surface 134, a shell attachment end 135, and a feed end 136 as further referenced in FIG. 13. It will be seen from an inspection of the noted figures that the shell attachment end 135 is fixedly secured a select shell edge. Outer strap surface 134 preferably comprises strap fastening means as generally referenced at 137. The feed end is fed through the strap-securing loop 132 about the user's lower leg for securing the posterior support shell 122 to the user's lower leg.

Alternatively, the present invention further contemplates an orthosis assembly for the treatment of plantar wounds comprising an L-shaped support member, an anterior support shell 135, at least two securing straps 136 as illustrated and referenced in FIG. 14. The L-shaped support member comprises posterior support shell 122 and plantar support platform 123. The anterior support shell 135 is designed for strapped attachment to the posterior support shell 122, the anterior support shell having an inner anterior support shell surface 137, an outer anterior support shell surface 138, and a plurality of strap-receiving loops 139 securely attached to the outer anterior support shell surface 138 as further referenced in FIG. 14. The anterior support shell is designed to receive the anterior, proximal portion of a user's lower leg. The securing straps 136 each comprise an inner strap surface 140, an outer strap surface 141, a shell attachment end 142, and a feed end 143 as further illustrated and referenced in FIG. 14. The shell attachment ends 142 are fixedly secured a select shell edge. The outer strap surfaces 141 preferably comprise strap fastening means. The feed ends 143 are fed through the strap-securing loops 139 and thus the anterior support shell 135 is secured to the proximal, anterior portion of the user's lower leg in fixed, weight-bearing relation.

Alternatively, the present invention contemplates an orthosis assembly for the treatment of plantar wounds comprising a pliable, substantially L-shaped support member 144 or leg-foot-receiving sleeve, as generally illustrated and referenced in FIG. 12; at least one rigid plantar support member 153; and at least one tie member 154. The L-shaped support member 144 preferably comprises a substantially vertical, leg support portion 145 and a substantially horizontal, foot support portion 146 as referenced in FIG. 12. The leg support portion 145 inherently has an inner leg portion surface, an outer leg portion surface, and first and second leg portion edges 147 as referenced in FIG. 12 and is sized and shaped to receive a user's lower leg 149 or distal portions thereof. The foot support portion 146 comprises first and second foot support edges 148 and is sized and shaped to support a user's foot 150 as generally depicted in FIG. 12. Notably, the foot support portion 146 comprises a superior insert-receiving surface 151 and an inferior ground-engaging surface 152 as further referenced in FIG. 12.

From a further inspection of FIG. 12, it will be seen that the assembly further comprises plantar support member 153, which is cooperatively received by the foot support portion 146 at the superior insert-receiving surface 151. The plantar support member 153 comprises a superior support surface (as referenced at 105), an inferior support surface (not specifically illustrated), and wound-protecting hollow 30. In this embodiment, the wound-protecting hollow 30 has a superior hollow surface and an inferior hollow surface, the superior hollow surface being continuous with the superior insert-receiving surface 151 and the inferior hollow surface being continuous with the inferior ground-engaging surface 152. The hollow 30 is spatially located for fitted placement in inferior adjacency to a user's plantar wound, the hollow 30 for transferring a user's weight away from the plantar wound thus facilitating plantar wound treatment. The tie member 154 is cooperatively associated with the first and second leg portion edges 147 and the first and second foot support edges 148 for securing the L-shaped support member 144 and the plantar support member 153 to the user's lower leg 149 and foot 150. Notably, the first and second leg portion edges 147 and the first and second foot portion edges 148 are located anteriorly.

The orthosis assembly for the treatment of plantar wounds may still further alternatively comprise at least one modified shoe, a leg support assembly, and at least one flexible select securing member. The modified shoe 155 is custom-fitted for receiving an orthotic insert, the modified shoe 155 comprising an inner insert-receiving surface and an outer upright-receiving surface as referenced in FIGS. 11(a) and 11(b). The orthotic insert is virtually identical to plantar support member 153 and has not been further illustrated.

The leg support assembly comprises rigid medial and lateral upright members 156 and a leg support portion 157 as further illustrated and referenced in FIGS. 11(a) and 11(b). Notably, the upright members 156 may be articulated adjacent the outer upright-receiving surface of modified shoe 155. The leg support portion 157 comprises an inner leg portion surface, an outer leg portion surface, a proximal end 158, a distal end 159, and first and second leg portion edges 160 as illustrated and referenced in FIG. 11(b). The leg support portion is sized and shaped to receive a portion of a user's lower leg. The upright members 156 extend proximally from the outer upright-receiving surface to points adjacent the proximal end 158. The flexible select securing member is cooperatively associated with the first and second leg portion edges 160 for securing the leg support portion 157 to the user's lower leg.

The select securing member may be selected from the group consisting of at least one tie member 154 and at least one securing strap 161, which strap is structured substantially as strap 120, 121, or 133 (which latter strap would necessarily include loop 132 fixedly mounted to the leg support portion 157. Each securing strap 161 comprises a fastening means surface, hook and loop fastening means, a support attachment end, and a strap engagement end. The support attachment end is fixedly secured to the leg support portion. The hook and loop fastening means are fixedly attached to the fastening means surface for securing the leg support portion 157 to the user's lower leg.

Still further, it is contemplated that the orthosis assembly for the treatment of plantar wounds may comprise a leg support assembly, a plantar support platform 102, and a proximal and distal support strap pairing. The leg support assembly comprises rigid medial and lateral upright members 163, both of which are illustrated and referenced in FIGS. 19-21. Each upright member 163 comprises an inner leg portion surface, an outer leg portion surface, a proximal end, and a distal end. The upright members are sized and shaped to receive lateral and medial portions of a user's lower leg.

The plantar support platform is substantially identical to platform 123. The proximal and distal support strap pairing comprise a proximal securing strap 164 and a distal securing strap 165 as illustrated and referenced in FIGS. 16-21. The securing straps 164 and 165 each comprise a fastening means surface and strap fastening means. The strap fastening means are fixedly attached to the fastening means surface for securing the leg support assembly about the user's lower leg. Notably, the medial and lateral upright members 163 may be articulatably attached to the plantar support platform 102 or 123 as generally depicted in FIGS. 16 and 17 at 166. Further, the upright members 163 may be sized and shaped to receive a distal portion of a user's lower leg as generally depicted in FIGS. 17 and 18.

While the above description contains much specificity, this specificity should not be construed as limitations on the scope of the invention, but rather as an exemplification of the invention. For example, as is described hereinabove, it is contemplated that the present invention discloses an orthotic accessory assembly for the treatment of diabetic plantar wounds; the orthotic accessory assembly essentially comprising a foot support portion sized and shaped to support a portion of a user's foot. The foot support portion inherently has a superior support surface, an inferior support surface, and at least one rigid, off-loading, wound-protecting hollow 30. The wound-protecting hollow comprises a superior hollow surface and an inferior hollow surface, the superior hollow surface being continuous with the superior support surface and the inferior hollow surface being continuous with the inferior support surface. The hollow is spatially located for fitted placement in inferior adjacency to a user's plantar wound, the hollow for transferring a user's weight away from the plantar wound thus facilitating plantar wound treatment.

The orthotic accessory assembly may further comprise leg securement means, the leg securement means being cooperatively associated with the user's lower leg for securing the foot support portion to the user's lower leg. The leg securement means may comprise a leg support portion, the leg support portion comprising an inner leg support surface, the leg support portion being sized and shaped to receive a portion of a user's lower leg, the leg support portion terminating proximally in an upper rim and terminating distally in a tarsal support structure, the tarsal support structure being cooperatively associated with the foot support portion, the upper rim being spatially located for fitted placement distal to the knee region of a user's lower leg. The foot support portion may be contoured to conform to the plantar surface of the user's foot, the foot support portion comprising a plurality of regions, the plurality of regions for supporting a plurality of foot regions of the user's foot.

The plurality of regions may be selected from a region grouping, the region grouping comprising a first anterior segment for supporting the toe region of the user's foot, a second anterior segment for supporting the metatarsal head region of the user's foot, an intermediate sole segment for supporting the arch region of the user's foot, and a posterior segment for supporting the heel region of the user's foot. The region grouping comprises a partial foot filler prosthesis, the partial foot filler prosthesis for filling space adjacent the user's foot (the user's foot being amputated at a point intermediate the toe region and heel region).

The lower leg support structure comprises select ankle support means, the select ankle support means being selected from the group consisting of ankle movement-enabling means and ankle movement-restricting means as earlier specified. The orthotic accessory assembly may further comprise select orthotic accessories, the select orthotic accessories being selected from the group consisting of at least one rigid upright assembly and at least one modified shoe. The modified shoe is custom-fitted for receiving the foot support portion and the leg support portion and the rigid upright assembly is cooperatively associated with the leg support portion and the foot support portion for providing select support reinforcing means. The select support reinforcing means are selected from the group consisting of ankle movement-enhancing means and ankle movement-preventing means.

Accordingly, although the invention has been described by reference to a preferred embodiment, it is not intended that the novel assembly be limited thereby, but that modifications thereof are intended to be included as falling within the broad scope and spirit of the foregoing disclosure, the following claims and the appended drawings.

I claim:

1. A method for manufacturing a custom-made orthosis for the treatment of plantar ulcers and foot deformities, comprising the steps of:
    taking a cast of the user's foot, to provide a replica or positive model of the user's foot;
    using the positive model to mold an orthosis including a substantially horizontal foot support structure sized and shaped to support a user's foot;
    grinding out an ulcer-protecting or foot deformity-protecting hollow, non-apertured portion in the shoe insole to accommodate a corresponding hollow in the orthosis, the hollow, non-apertured portion existing prior to any deformation caused by pressure exerted by the foot on the hollow portion, the hollow being located to correspond to a location of a plantar ulcer or other foot deformity on the user's foot, so that wearing the orthosis will reduce pressure on the plantar ulcer or other foot deformity when the user is standing or walking; and
    fitting the orthosis to a modified shoe.

2. The method of claim 1, wherein the step of taking a cast includes the step of taking a cast of the user's lower leg and foot, to provide a replice or positive model of the user's lower leg and foot, and wherein the step of using the positive model to mold includes molding a substantially L-shaped support member comprising the orthosis which includes: a substantially vertical lower leg support structure sized and shaped to receive a portion of the user's lower leg, and the substantially horizontal foot support structure sized and shaped to support the user's foot.

3. The method of claim 2, wherein the substantially vertical lower leg support structure comprises a substantially vertical, posterior support shell portion, and an anterior support shell portion connected to posterior support shell portion, and further comprising the step of securing an anterior support shell portion covering a portion of the user's lower leg to the vertical lower leg support structure.

4. The method of claim 2, wherein the lower leg support structure and the foot support structure are constructed using a lamination process, and constructed from a polyester and/or acrylic resin.

5. The method of claim 2, wherein the lower leg support structure and the foot support structure are constructed using a modified shoe and a leather calf structure held in place by metal uprights to provide solid or adjustable ankle joints.

6. The method of claim 2, wherein the lower leg support structure further comprises select ankle support means, the select ankle support means being selected from the group consisting of ankle movement-enabling means and ankle movement-restricting means.

7. The method of claim 1, wherein the substantially horizontal foot support structure includes a plantar support platform portion, and further comprising the step of attaching heel or sole wedges, laterally or medially or both, in distal adjacency to an inferior surface of the plantar support platform portion.

8. The method of claim 1, further comprising the step of forming a check socket from the positive model, the check socket constituting a preliminary form for the substantially horizontal foot support structure.

9. The method of claim 8, wherein the check socket is formed of clear plastic, providing a visual opportunity to make a detailed inspection of the plantar portion of the user's foot, and to note problematic portions of the check socket in relation to the positive model.

* * * * *